(12) United States Patent
Hodgkinson et al.

(10) Patent No.: US 12,285,444 B2
(45) Date of Patent: Apr. 29, 2025

(54) MULTICISTRONIC MIRNA DELIVERY FOR CARDIAC REPROGRAMMING

(71) Applicant: Duke University, Durham, NC (US)

(72) Inventors: Conrad P. Hodgkinson, Durham, NC (US); Victor J. Dzau, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 17/541,917

(22) Filed: Dec. 3, 2021

(65) Prior Publication Data

US 2022/0175845 A1  Jun. 9, 2022

Related U.S. Application Data

(60) Provisional application No. 63/122,785, filed on Dec. 8, 2020.

(51) Int. Cl.
*A61K 35/33* (2015.01)
*C12N 5/077* (2010.01)
*C12N 15/113* (2010.01)

(52) U.S. Cl.
CPC ............ *A61K 35/33* (2013.01); *C12N 5/0657* (2013.01); *C12N 15/113* (2013.01); *C12N 2310/141* (2013.01); *C12N 2320/31* (2013.01); *C12N 2501/65* (2013.01); *C12N 2501/999* (2013.01); *C12N 2506/1307* (2013.01)

(58) Field of Classification Search
CPC .... A61K 35/33; C12N 5/0657; C12N 15/113; C12N 2310/141; C12N 2320/31; C12N 2501/65; C12N 2501/999; C12N 2506/1307
See application file for complete search history.

(56) References Cited

U.S. PATENT DOCUMENTS

2018/0066285 A1 * 3/2018 Ojala ................ C12N 15/74

FOREIGN PATENT DOCUMENTS

WO    WO-2021007515 A1 * 1/2021 ........... A61K 48/005

OTHER PUBLICATIONS

Heidersbach et al., eLife. 2013; 2: e01323, p. 1-22. (Year: 2013).*
Heidenreich et al., Interdisciplinary Council on Quality of, C., and Outcomes, R. (2011) Forecasting the future of cardiovascular disease in the United States: a policy statement from the American Heart Association. Circulation 123, 933-944.
Fan et al, (2012) Cardiac fibroblasts, fibrosis and extracellular matrix remodeling in heart disease. Fibrogenesis Tissue Repair 5, 15.
Hodgkinson et al., (2015) MicroRNAs and Cardiac Regeneration. Circ Res 116, 1700-1711.
Dal-Pra et al., (2014) Reprogramming approaches in cardiovascular regeneration. Curr Treat Options Cardiovasc Med 16, 327.
Qian et al., (2013) Reprogramming of mouse fibroblasts into cardiomyocyte-like cells in vitro. Nat Protoc 8, 1204-1215.
Nam et al., (2014) Induction of diverse cardiac cell types by reprogramming fibroblasts with cardiac transcription factors. Development 141, 4267-4278.
Jayawardena et al., (2012) MicroRNA-mediated in vitro and in vivo direct reprogramming of cardiac fibroblasts to cardiomyocytes. Circ Res 110, 1465-1473.
Jayawardena et al., (2015) MicroRNA induced cardiac reprogramming in vivo: evidence for mature cardiac myocytes and improved cardiac function. Circ Res 116, 418-424.
Hodgkinson et al., (2018) Cardiomyocyte Maturation Requires TLR3 Activated Nuclear Factor Kappa B. Stem Cells 36, 1198-1209.
Qian et al., (2012) In vivo reprogramming of murine cardiac fibroblasts into induced cardiomyocytes. Nature 485, 593-598.
Song et al., (2012) Heart repair by reprogramming non-myocytes with cardiac transcription factors. Nature 485, 599-604.
Okita et al., (2007) Generation of germline-competent induced pluripotent stem cells. Nature 448, 313-317.
Papapetrou et al, (2009) Stoichiometric and temporal requirements of Oct4, Sox2, Klf4, and c-Myc expression for efficient human iPSC induction and differentiation. Proc Natl Acad Sci U S A 106, 12759-12764.
Wang et al., (2015) Stoichiometry of Gata4, Mef2c, and Tbx5 influences the efficiency and quality of induced cardiac myocyte reprogramming. Circ Res 116, 237-244.
Milone et al., (2018) Clinical use of lentiviral vectors. Leukemia 32, 1529-1541.
Chamberlain et al., (2017) Cardiac gene therapy with adeno-associated virus-based vectors. Curr Opin Cardiol.
McCarty et al., (2008) Self-complementary AAV vectors; advances and applications. Mol Ther 16, 1648-1656.
Yang et al., (2010) Inhibition of hepatitis C virus replication using adeno-associated virus vector delivery of an exogenous anti-hepatitis C virus microRNA cluster. Hepatology 52, 1877-1887.
Jayawardena et al., (2014) Direct reprogramming of cardiac fibroblasts to cardiomyocytes using microRNAs. Methods Mol Biol 1150, 263-272.
Altuvia et al., (2005) Clustering and conservation patterns of human microRNAs. Nucleic Acids Res 33, 2697-2706.
Lu et al., (2007) Transgenic over-expression of the microRNA miR-17-92 cluster promotes proliferation and inhibits differentiation of lung epithelial progenitor cells. Dev Biol 310, 442-453.

(Continued)

*Primary Examiner* — Taeyoon Kim
*Assistant Examiner* — Jianjian Zhu
(74) *Attorney, Agent, or Firm* — Nutter McClennen & Fish LLP (57) ABSTRACT

The invention provides a method of promoting reprogramming of a cardiac fibroblast into a cardiomyocyte by contacting the cardiac fibroblast with an isolated polynucleotide molecule comprising at least two functional miRNA sequences using a multicistronic expression system for reprogramming of fibroblasts into functional mature cardiomyocytes.

11 Claims, 4 Drawing Sheets

Specification includes a Sequence Listing.

(56) References Cited

OTHER PUBLICATIONS

Mogilyansky et al., (2013) The miR-17/92 cluster: a comprehensive update on its genomics, genetics, functions and increasingly important and numerous roles in health and disease. Cell Death Differ 20, 1603-1614.

Tiemann et al., (2011) Optimal reprogramming factor stoichiometry increases colony Nos. and affects molecular characteristics of murine induced pluripotent stem cells. Cytometry A 79, 426-435.

Carey et al., (2011) Reprogramming factor stoichiometry influences the epigenetic state and biological properties of induced pluripotent stem cells. Cell Stem Cell 9, 588-598.

Altschul, S., et al., "Basic Local Alignment Search Tool," Journal of Molecular Biology vol. 215, 1990, pp. 403-410.

Devereux, J., et al., "A comprehensive set of sequence analysis programs for the VAX," Nucleic Acids Research vol. 12, No. 1, 1984, pp. 387-395.

* cited by examiner

SEQUENCE LISTING

```
<160> NUMBER OF SEQ ID NOS: 9

<210> SEQ ID NO 1
<211> LENGTH: 84
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: miR-17

<400> SEQUENCE: 1
gucagaauaa ugucaaagug cuuacagugc agguagugau gugugcaucu acugcaguga    60
gggcacuugu agcauuaugc ugac                                          84

<210> SEQ ID NO 2
<211> LENGTH: 96
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: miR-18a

<400> SEQUENCE: 2
ugcgugcuuu uuguucuaag gugcaucuag ugcagauagu gaaguagacu agcaucuacu    60
gcccuaagug cuccuucugg cauaagaagu uauguc                             96

<210> SEQ ID NO 3
<211> LENGTH: 82
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: miR-19a

<400> SEQUENCE: 3
gcagcccucu guuaguuuug cauaguugca cuacaagaag aauguaguug ugcaaaucua    60
ugcaaaacug augguggccu gc                                            82

<210> SEQ ID NO 4
<211> LENGTH: 107
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: miR-20a

<400> SEQUENCE: 4
gugugaugug acagcuucug uagcacuaaa gugcuuauag ugcagguagu guguagccau    60
cuacugcauu acgagcacuu aaaguacugc cagcuguaga acuccag                107

<210> SEQ ID NO 5
<211> LENGTH: 87
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
```

```
<223> OTHER INFORMATION: miR-19b

<400> SEQUENCE: 5
cacuggucua ugguuaguuu ugcagguuug cauccagcug uauaauauuc ugcugugcaa    60
auccaugcaa aacugacugu gguggug                                       87

<210> SEQ ID NO 6
<211> LENGTH: 22
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: miR-1

<400> SEQUENCE: 6
uggaauguaa agaaguaugu au                                            22

<210> SEQ ID NO 7
<211> LENGTH: 22
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: miR-133

<400> SEQUENCE: 7
uuuggucccc uucaaccagc ug                                            22

<210> SEQ ID NO 8
<211> LENGTH: 22
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: miR-208

<400> SEQUENCE: 8
auaagacgag caaaaagcuu gu                                            22

<210> SEQ ID NO 9
<211> LENGTH: 21
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: miR-499

<400> SEQUENCE: 9
uuaagacuug cagugauguu u                                             21
```

MULTICISTRONIC MIRNA DELIVERY FOR CARDIAC REPROGRAMMING

RELATED APPLICATIONS

This application claims the benefit of priority under 35 U.S.C. § 119(e) to U.S. Provisional Application No. 63/122,785, filed Dec. 8, 2020, the entire contents of which is incorporated herein by reference in its entirety.

STATEMENT AS TO RIGHTS TO INVENTIONS MADE UNDER FEDERALLY SPONSORED RESEARCH AND DEVELOPMENT

This invention was made with Government support under Grant No. 1R01HL131814-01A1 awarded by the National Institutes of Health. The Government has certain rights in this invention.

SEQUENCE LISTING

The Sequence Listing written in file 035327-532001US_Sequence_Listing_ST25.txt, created Dec. 3, 2021, 2,821 bytes, machine format IBM-PC, MS Windows operating system, is hereby incorporated by reference.

SUMMARY OF THE INVENTION

In one aspect, the present disclosure provides a method of promoting reprogramming of a cardiac fibroblast into a cardiomyocytes by contacting the cardiac fibroblast with an isolated polynucleotide molecule comprising at least two functional miRNA sequences selected from the group consisting of miR-1, miR-133, miR-208, and miR-499. Such functional miRNA sequences may comprises at least 20%, 25%, 30%, 35%, 40%, 45%, 50%, 55%, 60%, 65%, 70%, 75%, 80%, 85%, 90%, 95%, 99%, or 100% identity to the sequences described herein for miR-1, miR-133, miR-208, and miR-499.

In another aspect, the present disclosure provides an isolated polynucleotide molecule comprising at least two functional miRNA sequences selected from the group consisting of miR-1, miR-133, miR-208, and miR-499. In some embodiments, the isolated polynucleotide molecule described herein further comprises at least two endogenous pre-miRNA sequences, wherein the mature miRNA sequence in each of the at least two endogenous pre-miRNA sequences are replaced by one of the at least two functional miRNA sequences. Such pre-miRNA sequences may comprises at least 20%, 25%, 30%, 35%, 40%, 45%, 50%, 55%, 60%, 65%, 70%, 75%, 80%, 85%, 90%, 95%, 99%, or 100% identity to the sequences described herein.

In another aspect, the present disclosure provides an expression vector comprising the isolated polynucleotide molecule described herein.

In another aspect, the present disclosure provides a use of the isolated polynucleotide molecule or the expression vector, as described herein for reprogramming a cardiac fibroblast into a cardiomyocytes.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The polynucleotide and polypeptide sequences disclosed herein are shown using standard letter abbreviations for nucleotide bases and amino acids as set forth in 37 CFR § 1.82), which incorporates by reference WIPO Standard ST.25 (1998), Appendix 2, Tables 1-6.

The term "percent identity" as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated using published techniques and widely available computer programs, such as the GCS program package (Devereux et al, *Nucleic Acids Res.* 12:387, 1984), BLASTP, BLASTN, FASTA (Atschul et al., *J Mol Biol* 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof. The amino acid substitution(s) may be a conservative amino acid substitution, for example at a non-essential amino acid residue in the CDR sequence(s). A "conservative amino acid substitution" is understood to be one in which the original amino acid residue is substituted with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "recombinant" nucleic acid molecule, polypeptide, and cell as used herein, refers to a nucleic acid molecule, polypeptide, and cell that has been altered through human intervention. As non-limiting examples, a recombinant nucleic acid molecule can be one which: 1) has been synthesized or modified in vitro, for example, using chemical or enzymatic techniques, or recombination of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence.

The term "vector" is used herein to refer to a nucleic acid molecule or sequence capable of transferring or transporting another nucleic acid molecule. For example, a vector can be used as a gene delivery vehicle to transfer a gene into a cell. The transferred nucleic acid molecule is generally linked to, e.g., inserted into, the vector nucleic acid molecule. Generally, a vector is capable of replication when associated with the proper control elements. The term "vector" includes cloning vectors and expression vectors, as well as viral vectors and integrating vectors. An "expression vector" is a vector that includes a regulatory region, thereby capable of expressing DNA sequences and fragments in vitro and/or in vivo. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. In some embodiments, a vector is a gene delivery vector.

It is understood that aspects and embodiments of the disclosure described herein include "comprising," "consisting," and "consisting essentially of" aspects and embodiments. As used herein, "comprising" is synonymous with "including", "containing", or "characterized by", and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

The term "reduce," "attenuate," "promote," or "increase" is meant to alter negatively or positively, respectively, by at least 5%. An alteration may be by 5%, 10%, 25%, 30%, 50%, 75%, 90%, 100%, or even more (for positive alterations).

By the terms "effective amount" and "therapeutically effective amount" of a formulation or formulation component is meant a sufficient amount of the formulation or component to provide the desired effect. For example, by "an effective amount" is meant an amount of an isolated polypeptide or polynucleotide to prevent, attenuate, and/or inhibit, a cancer (e.g., preventing, attenuating, and/or inhibiting the proliferation of a cancer cell) in a subject. Ultimately, the attending physician or veterinarian decides the appropriate amount and dosage regimen.

As used herein, a "purified" protein refers to a protein (such as bovine serum albumin) that has been separated from all other cellular and serum components, such as, but not limited to, other proteins, carbohydrates, lipids, cholesterol, etc. "Purified" proteins have been purified to a level of purity not found in nature and are suitable for clinical use and in the context of ex vivo cell therapy. Purity is measured by any appropriate standard method, for example, by column chromatography, thin layer chromatography, or high-performance liquid chromatography (HPLC) analysis.

All polynucleotides (e.g., microRNAs), polypeptides, amino acids, or other compositions or compounds used in the cell culture medium of the invention are purified and/or isolated. Specifically, as used herein, an "isolated" or "purified" nucleic acid molecule is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally occurring state. Purified also defines a degree of sterility that is safe for administration to a human subject, e.g., lacking infectious or toxic agents.

As used herein, the term "at least one miRNA" or "miR-combo" refers to any mixture (e.g., one or more than one) of miRNA molecules capable of facilitating the reprogramming of cells (such as, but not limited fibroblasts, for example cardiofibroblasts) into cardiomyocytes.

The terms "treating," "treat," and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a sufficient amount of the formulation or component to provide the desired effect. For example, by "an effective amount" is meant an amount of a microRNA and/or reprogramming media to directly reprogram cells (such as fibroblasts, e.g., cardiac fibroblasts) to cardiomyocytes in a subject. Ultimately, the attending physician or veterinarian decides the appropriate amount and dosage regimen.

The methods and compositions of the invention are associated with clinical advantages over previous methods. Combinations of specific miRNAs (miR combo) or transcription factors (GMT) convert fibroblasts into cardiomyocytes and improve cardiac function. These reprogramming factors have been delivered into the heart via *lenti-* or retro-viruses. Such viruses are less than ideal as neither specifically target fibroblasts. Moreover, each reprogramming factor was delivered into the heart individually. Thus, prior to the invention, it was impossible to ensure that each cell received all of the reprogramming factors. The invention provides a solution to this problem.

The compositions are administered as pharmaceutically acceptable compositions, e.g., formulated with a pharmaceutically acceptable carrier or excipient. For in vivo uses, the amounts and routes of administration will depend on numerous factors, including the amount of cardiofibroblast cells to be reprogrammed, severity of tissue damage, means of administration, and the like. In some examples, the miR combo is directly injected into the heart of the subject. In such embodiments, the amount needed may be about 1 mL, 2 mL, 3 mL, 4 mL, 5 mL mL to 10 mL, 20 mL, 30 mL, 40 mL, 50 mL, 60 mL, 70 mL, 80 mL, 90 mL, 100 mL or more, inclusive of values falling in between these numbers. In other embodiments, the miR combo solution may be administered via lavage (e.g., soaking the heart of the subject). In such embodiments, the amount of solution needed may be about 1 L, 2 L, 3 L, 4 L, 5 L or more, inclusive of values falling in between these numbers. In general, an exemplary dosage is from 0.01 µg to 100 g per kg of body weight, from 0.1 µg to 10 g per kg of body weight, from 1.0 µg to 1 g per kg of body weight, from 10.0 µg to 100 mg per kg of body weight, from 100 µg to 10 mg per kg of body weight, or from 1 mg to 5 mg per kg of body weight, and may be given once or more daily, weekly, monthly or yearly. Examples of dosages based on small animal studies are in the range of 80 mg/kg for single or multiple dosages. However, it is expected with appropriate modification dosages 1-25 mg/kg for single to three repeated dosages will confer clinical benefit in human subjects.

In some embodiments, the cardiac fibroblast is contacted with a combination of four miRNAs comprising miR-1, miR-133, miR-208, and miR-499. For example, the cardiac fibroblast is contacted with a combination of four miRNAs consisting essentially of miR-1, miR-133, miR-208, and miR-499. For clinical treatment of a patient, the cardiac fibroblast is contacted with the isolated polynucleotide molecule in vivo. For example, the cardiac fibroblast is present in a human subject diagnosed with impaired cardiac function or in a human subject diagnosed with the presence of cardiac scar tissue.

In an exemplary therapeutic construct, the isolated polynucleotide molecule comprises a multicistronic system to express two or more miRNA sequences selected from the group consisting of miR-1, miR-133, miR-208, and miR-499. For example, the multicistronic system is expressed in cardiac-tropic adeno-associated virus (AAV)-based vector, e.g., AAV1.

As shown in the example described below, reprogramming efficiency was improved by specifically targeting fibroblasts and by ensuring that each reprogramming factor was expressed in the cell. To that end, a multicistronic system to express all four miRNAs of miR combo from a single viral genome was developed. The order of the miRNAs in the multicistronic construct gave rise to different levels of miRNA expression in cultured mouse fibroblasts. A combination that resulted in equivalent expression levels of each of the four miRNAs of miR combo showed the highest reprogramming efficiency. To directly target fibroblasts, several AAV serotypes were screened. AAV1 displayed tropism towards cardiac fibroblasts. Combining multicistronic expression with AAV1 delivery enhanced cardiac reprogramming in vivo. The data described herein indicate that multicistronic expression with AAV1 delivery is useful to treat mammalian subjects, e.g., humans, to reverse cardiac scars (fibrosis), e.g., convert fibroblasts into cardiomyocytes, to improve cardiac function. The subject to be treated has been diagnosed as comprising cardiac scars (fibrosis) present in the heart muscle, e.g., using methods known in the art, e.g., cardiac imaging methodology and/or cardiac function tests reflecting reduced cardiac function after myocardial infarction or other damage to the heart muscle. The methods are of great clinical benefit to subjects who have experienced cardiac infarction or other cardiac conditions or events that have led to cardiac scars/fibrosis.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

BRIEF DESCRIPTION OF THE DRAWINGS

FIG. 2 is a set of graphs showing that miRNA stoichiometry influences reprogramming efficiency. (A) Neonatal cardiac fibroblasts were transiently transfected with a plasmid containing one of the four constructs of the multicistronic miR combo. After 3 days, miRNA expression was analyzed by qPCR. Expression of each miRNA is shown relative to expression levels in fibroblasts transfected with a construct containing five identical copies of a non-targeting miRNA. N=3 (B) Cultured neonatal cardiac fibroblasts were transiently transfected with the four constructs of the multicistronic miR combo in vitro. Following transfection, expression levels of the cardiac commitment marker Mef2C (day 3 post-transfection) and the mature cardiomyocyte marker aMHC (day 14 post-transfection) were measured by qPCR. Expression is shown relative to expression levels in fibroblasts transfected with a construct containing five identical copies of a non-targeting miRNA. N=3.

FIG. 3 is a set of graphs showing that AAV1 demonstrates fibroblast tropism. (A) Cardiac fibroblasts were incubated with an AAV GFP reporter at a wide range of genome copies (GC) per cell. AAV1, 2, 5, 6, 9, and rh10 capsids were used. Imaging and FACS was performed 8 days following infection. Images 160,000 GC/cell. FACS AAV1 10,000 and 160,000 GC/cell shown N=3. (B) Comparison of the number of cardiac fibroblasts and cardiomyocytes expressing the GFP transgene following incubation with 160,000 genome copies per cell using the indicated capsids. GFP+ cells were counted by FACS 8 days following infection N=3. (C) AAV1-GFP was injected into mouse hearts. Three weeks following injection heart sections were immunostained for GFP and the fibroblast marker S100A4. Representative images are shown from three mice per group.

DETAILED DESCRIPTION OF THE INVENTION

Injury to the human heart results in an irreversible loss of cardiomyocytes. In their place, fibroblasts fill the dead tissue and through various processes form a scar (1,2). The loss of cardiomyocytes and replacement by scar impair heart function and eventually lead to cardiac failure(2). It has been shown that converting cardiac fibroblasts within the scar tissue into cardiomyocytes by administration of combinations of specific transcription factors or miRNAs improves heart function (3,4). However, the effects are relatively modest due to the relatively low rate of conversion related to the low efficiency and lack of optimization of delivery of the combined reprogramming factors. The methods disclosed herein provide a solution to the clinical problem of non-functional scar tissue in an organ such as the heart following injury or disease.

Currently, there are two demonstrated methods for converting scar fibroblasts into cardiomyocytes in vivo. The Srivastava and Olsen laboratories focused their approach on transcription factors implicated in cardiac development. Screening combinations of these cardiac development transcription factors identified that the combination of Gata4 (G), Mef2C (M), and Tbx5 (T) induced fibroblast conversion to cardiomyocytes (5,6). In contrast to the transcription factor approach, combinations of miRNAs that are highly expressed in cardiac muscle were screened to show that a combination of four miRNAs (miR-1, miR-133, miR-208, and miR-499), which was termed "miR combo", induced fibroblast conversion into mature cardiomyocytes in vitro and in vivo (7-9). Currently both GMT and miR combo are delivered in vivo via pooled lenti-/retro-viruses, each expressing one of the individual reprogramming factor (8,10,11). This approach leads to widely different expression ratios between each reprogramming factor in every transduced fibroblast. Moreover, lenti- and retro-viruses are promiscuous and will infect any cell that is undergoing proliferation. The inability to control reprogramming factor stoichiometry and cellular targeting may explain the relatively low conversion rate observed in vivo.

The reprogramming of somatic cells is widely acknowledged as an inefficient process (12). Balanced expression of reprogramming factors is crucial and improved efficiency is dependent on their relative ratios and optimal stoichiometry (13). Direct reprogramming of fibroblasts into cardiomyocytes by transcription factors was improved following their administration using a precise dosage and stoichiometry (14). By delivering a single transgene containing all reprogramming factors, a multicistronic system resulted in the precise relative expression of factors that resulted in improved reprogramming efficiency.

In vivo cardiac reprogramming by miR combo has been demonstrated using 4 individual lentiviral vectors delivering the individual miRNAs of miR combo (7-9). The advantages of lentiviral vectors are their efficient transduction of many cell types, and rapid, long-term transgene expression following transduction (15). Their limitations are integration of the transgene into the host genome resulting in possible insertional mutagenesis, and the immunogenicity associated with the lentiviral vector envelope (15). Adeno-associated viruses (AAVs) have recently emerged as one of the most promising vectors used in cardiac gene therapy due to their lack of insertion and existence as episomes, the absence of immunogenicity compared to other viral vectors, and tropism for certain tissues with the capsid serotypes 1, 6, and 9 demonstrating the greatest potential for transducing cardiac cells (16). Although the genome capacity of AAV is limited to ~5 kb, their small size means most miRNA genes and clusters can be accommodated. Because the AAV genome is single-stranded, the conversion to double-stranded DNA for transcription can delay transgene expression. This is mitigated by using self-complementary sequences which package an inverted complementary sequence that folds into double-stranded DNA before transcription (17).

A delivery system was developed to ensure fibroblasts were efficiently targeted and expressed all four constituent miRNAs of miR combo. To ensure expression of all four constituent miRNAs, a multicistronic system was developed. The order of each miRNA in the multicistronic construct gave rise to different levels of miRNA expression. The combination that resulted in equivalent expression levels of each of the four miRNAs of miR combo demonstrated the highest reprogramming efficiency. Furthermore, to enhance cell selectively, the ability of various AAV serotypes to specifically target fibroblasts was measured. One serotype, AAV1, displayed fibroblast troism. Combining AAV1 with multicistronic miR combo led to robust and efficient conversion of fibroblasts into cardiomyocytes in vivo.

AAV Vector Delivery Methods for Cardiac Reprogramming Therapy

Delivery of AAV vectors to the myocardium can be broadly divided into two approaches 1) direct intramyocardial injection and 2) transvascular administration.

Intramyocardial Injection

Direct intramyocardial injection has several advantages: 1) the virus can be delivered at a very high local concentration, 2) direct injection bypasses the endothelial barrier, which is a formidable hurdle for efficient gene transfer, 3) off-target organ transduction is minimized, though not eliminated and 4) the neutralizing effect of pre-existing antibodies is stunted. Intramyocardial injection can be done via direct injection after thoracotomy, which offers the greatest flexibility and precision of injection. Percutaneous, catheter based injections are minimally invasive.

Transvascular Delivery

A recombinant AAV vector may also be injected peripherally, e.g., using AAV vectors with cardiac tropism.

Antegrade Intracoronary Injection

Antegrade intracoronary infusion of AAV vectors may also be used, e.g., percutaneous access to the coronaries is routinely performed during angioplasty. Because of its minimally invasive nature, antegrade intracoronary injection has been used to deliver therapeutic AAV vectors clinically.

Retrograde Injection

Retrograde injection delivery approach may be also be used. For example, this approach may result in longer dwell times of the vector the coronary vasculature.

Molecular Cardiac Surgery with Recirculating Delivery (MCARD)

This approach involves a subject being put on cardiopulmonary bypass, thereby allowing the complete isolation of the cardiac circulation from the systemic blood circulation and the recirculation of vector-containing blood exclusively through the cardiac circulation. This system has several advantages: 1) it allows the prolonged circulation of the AAV vector containing the therapeutic transgene through the coronary system, 2) the closed nature of the system might allow its use in patients with pre-existing antibodies and 3) off-target transduction is reduced because the system can be flushed from remaining vector before completion of the coronary bypass. MCARD is an invasive method that is likely only applicable in situations where an on-pump coronary bypass surgery or valve surgery is required.

Example 1: Multicistronic miRNA Delivery for Cardiac Reprogramming

Abstract

Following heart injury, cardiomyocytes, are lost and are not regenerated. In their place, fibroblasts invade the dead tissue where they generate a scar, which reduces cardiac function. It has been demonstrated that combinations of specific miRNAs (miR combo) or transcription factors (GATA4, MEF2c, TBX5; GMT), delivered by individual lenti-/retro-viruses in vivo, can convert fibroblasts into cardiomyocytes and improve cardiac function. However, the effects are relatively modest due to the low efficiency of delivery of miR combo or GMT. Moreover, neither lenti- nor retro-virus are specific for fibroblasts. The efficiency was improved by optimizing delivery. In the first instance, a multicistronic system was developed to express all four miRNAs of miR combo from a single viral genome. The order of the miRNAs in the multicistronic construct gave rise to different levels of miRNA expression in cultured mouse fibroblasts. A combination that resulted in equivalent expression levels of each of the four miRNAs of miR combo showed the highest reprogramming efficiency. To directly target fibroblasts, several AAV serotypes were screened and demonstrated that AAV1 displayed tropism towards cardiac fibroblasts. Combining multicistronic expression with AAV1 delivery enhanced cardiac reprogramming in vivo.

Methods

Generation of multicistronic miR combo: The endogenous multicistronic miR17-92 (NCBI database (NT_009952.14) was used as a scaffold to generate the multicistronic miR combo constructs. The multicistronic miR combo constructs were generated from the miR-17-92 cassette according to Yang et al (18). Lower stems and loops (~11 bp) of the endogenous miRNAs, as well as all intervening sequences and the 5' (91 bp) and 3' flanking (18 bp) sequences, were all maintained. Sequences of the endogenous pre-miRNAs are shown below; sequences in italics were replaced with the miRNAs of miR combo:

```
SEQ ID NO: 1: miR-17
5'GUCAGAAUAAUGUCAAAGUGCUUACAGUGCAGGUAGUGAUGUGUGCAU

CUACUGCAGUGAGGGCACUUGUAGCAUUAUGCUGAC3'

SEQ ID NO: 2: miR-18a
5'UGCGUGCUUUUUGUUCUAAGGUGCAUCUAGUGCAGAUAGUGAAGUAGA

CUAGCAUCUACUGCCCUAAGUGCUCCUUCUGGCAUAAGAAGUUAUGUC3'

SEQ ID NO: 3: miR-19a
5'GCAGCCCUCUGUUAGUUUUGCAUAGUUGCACUACAAGAAGAAUGUAGU

UGUGCAAAUCUAUGCAAAACUGAUGGUGGCCUGC3'

SEQ ID NO: 4: miR-20a
5'GUGUGAUGUGACAGCUUCUGUAGCACUAAAGUGCUUAUAGUGCAGGUA

GUGUGUAGCCAUCUACUGCAUUACGAGCACUUAAAGUACUGCCAGCUGU

AGAACUCCAG3'

SEQ ID NO: 5: miR-19b
5'CACUGGUCUAUGGUUAGUUUUGCAGGUUUGCAUCCAGCUGUAUAAUAU

UCUGCUGUGCAAAUCCAUGCAAAACUGACUGUGGUGGUG3'
```

Sequences employed for the constituent miRNAs of miR combo were:

```
SEQ ID NO: 6: miR-1:
5'UGGAAUGUAAAGAAGUAUGUAU3'

SEQ ID NO: 7: miR-133:
5'UUUGGUCCCCUUCAACCAGCUG3'

SEQ ID NO: 8: miR-208:
5'AUAAGACGAGCAAAAAGCUUGU3'

SEQ ID NO: 9: miR-499:
5'UUAAGACUUGCAGUGAUGUUU3'
```

All constructs were generated by GenScript and were supplied on the pcDNA3.1 plasmid vector backbone.

Transient transfection with miRNAs or plasmid-DNA: Mouse (C57BL/6) neonatal cardiac fibroblasts were isolated from 2 day old mouse neonates according to the method outlined in Jayawardena et al (19). Following isolation fibroblasts were cultured in growth media containing DMEM (ATCC, Catalogue number 30-2002) supplemented with 15% v/v FBS (Thermo Scientific Hyclone Fetal bovine serum, Catalogue number SH30071.03, Lot number AXK49952) and 1% v/v penicillin/streptomycin (Gibco, Catalogue number 15140-122, 100 units Penicillin, 100 µg/ml Streptomycin). Fibroblasts were passaged once the cells had reached 70-80% confluence using 0.05% w/v trypsin (Gibco, Catalogue number 25300-054). Freshly isolated fibroblasts were labelled as Passage 0. Experiments were conducted with cells at passage 2. For all experiments, cells were seeded at 5000 cells/cm$^2$ in growth media and transfected 24 hours later.

MiR combo transfection: On the day of transfection, 5 nmol of miRNA (non-targeting control or miR combo) was diluted in serum-free DMEM media (final volume 150 µl). In a separate tube Dharmafect-I (ThermoScientific) was diluted in serum-free DMEM media (1.5 µl Dharmafect-I in a total of 150 µl volume for each well). After 5 minutes incubation at room temperature the miRNA and Dharmafect-I complexes were mixed together. After twenty minutes at room temperature they were added to the cells and complete media added to total volume of 550 µl per well. One day after transfection, complexes were removed and the cells cultured in growth media for the duration of the experiment.

Plasmid-DNA: On the day of transfection, 0.5 µg of each plasmid containing the multicistronic miR combo construct was diluted in Plus reagent (1.5 µl, ThermoFisher) and serum-free DMEM (total volume 50 µl). In a separate reaction, LTX reagent (1.5 µl, ThermoFisher) was diluted in serum-free DMEM (48.5 µl). After five minutes at room temperature, the reactions were combined, mixed and left for a further twenty minutes at room temperature. The complexes were added to cells and complete media added to total volume of 550 µl per well. One day after transfection, complexes were removed and the cells cultured in growth media for the duration of the experiment.

Generation of self-complementary adeno-associated virus (scAAV): scAAV was generated by sub-cloning the CMV promoter, miR combo construct 1, and the BGH polyadenylation sequence from the pcDNA3.1 plasmid into the MCS of the tr1TR2-Basic (+) plasmid (Addgene). Viral particles were generated by Vector Biolabs.

Quantitative PCR: miRNA: miRNAs were isolated with a MirVana Isolation kit (ThermoFisher) according to the manufacturer's protocol. Expression of the miRNAs was determined in a standard qPCR reaction involving FAM conjugated specific primers (ThermoFisher) and TaqMan Gene Expression Master Mix. Briefly, miR combo expression levels were measured by absolute quantification using the Standard Curve Method. Reverse transcription products (cDNA) from miR precursor mimics to miR-1, miR-133, miR-208, and miR-499 (Ambion) were serially diluted and qPCR was performed to generate standard curves to correct for differences in primer efficiencies. Assay ID numbers for the primers employed: miR-1 477820_mir; miR-133 rno480920_mir; miR-208 477819_mir; miR-499 rno481402_mir. RNA: Total RNA was extracted using Quick-RNA MiniPrep Kit according to the manufacturer's instructions (Zymo Research). Total RNA (50 ng-100 ng) was converted to cDNA using a high capacity cDNA reverse transcription kit (Applied Biosystems). cDNA was used in a standard qPCR reaction involving FAM conjugated gene specific primers (ThermoFisher) and TaqMan Gene Expression Master Mix (ThermoFisher). Primers were acquired from ThermoFisher and the assay ID numbers are: Mef2C Mm01340842_m1; Myh6 Mm00440359_m1.

Mice, Myocardial Infarction and Virus Injection: Adult male (8 week old) fibroblast-specific protein 1 Cre-tandem dimer Tomato (tdTomato) mice were subjected to permanent ligation of the left anterior descending coronary artery. AAV (AAV2/1) containing construct 1 (GenScript) of the multicistronic miR combo ($10^{11}$ viral particles) were injected at 2 sites 2 mm below the site of ligation. An AAV (AAV2/1) containing a non-targeting miRNA was used as a control.

Immunocytochemistry: Hearts were removed 2 months after injection and fixed in formalin. After sectioning, sections were stained with antibodies for cardiac troponin-T (Abcam) and tdTomato (Abcam). Confocal images were captured using an LSM 510 Meta DuoScan microscope (Zeiss) and processed using LSM 5 software, version 4.2.

Results & Discussion

The data described herein was to generate a single delivery system for efficient reprogramming of cardiac fibroblasts into cardiomyocytes in vivo.

Current in vivo cardiac reprogramming strategies utilize independent vectors; with each vector carrying a single reprogramming factor. This is inefficient as it is impossible to ensure that each reprogramming factor will enter the cell. Moreover, it is impossible to control the relative amount of each reprogramming factor in each cell. Consequently, to ensure that each cell expressed all of the reprogramming factors at a defined stoichiometry, a multicistronic expression system was developed. The combination of four miRNAs (miR-1, miR-133, miR-208 and miR-499), also known as "miR combo", which has been demonstrated to reprogram fibroblasts into functional mature cardiomyocytes (7), were used for the expression system.

Figure 1:
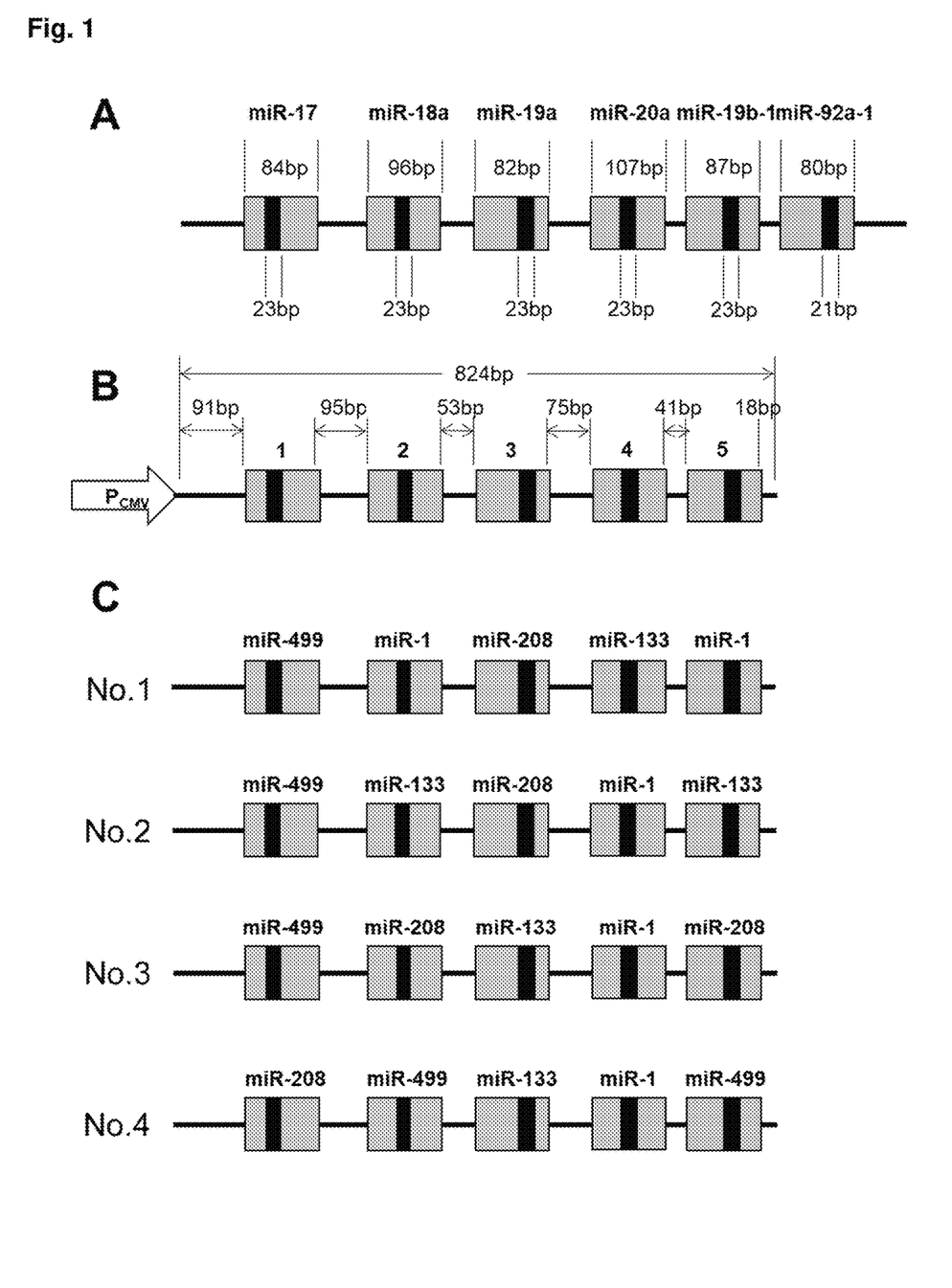
FIG. 1 is a set of graphs showing generation of a multicistronic miR combo. (A) The endogenous miR-17-92 multicistronic. Pre-miRNAs (grey boxes) and mature miRNAs (black boxes) are shown. (B) Generation of the multicistronic miR combo: The sequences for the mature endogenous miRNAs were replaced with the mature miRNA sequences of the constituent miRNAs of miR combo. As indicated in the figure, lower stems and loops of the endogenous miRNAs as well as the spacing between the endogenous miRNAs were maintained. The region occupied by miR-92a-1 was not used and was removed. (C) Constructs of the multicistronic miR combo used in this study.
Figure 2:
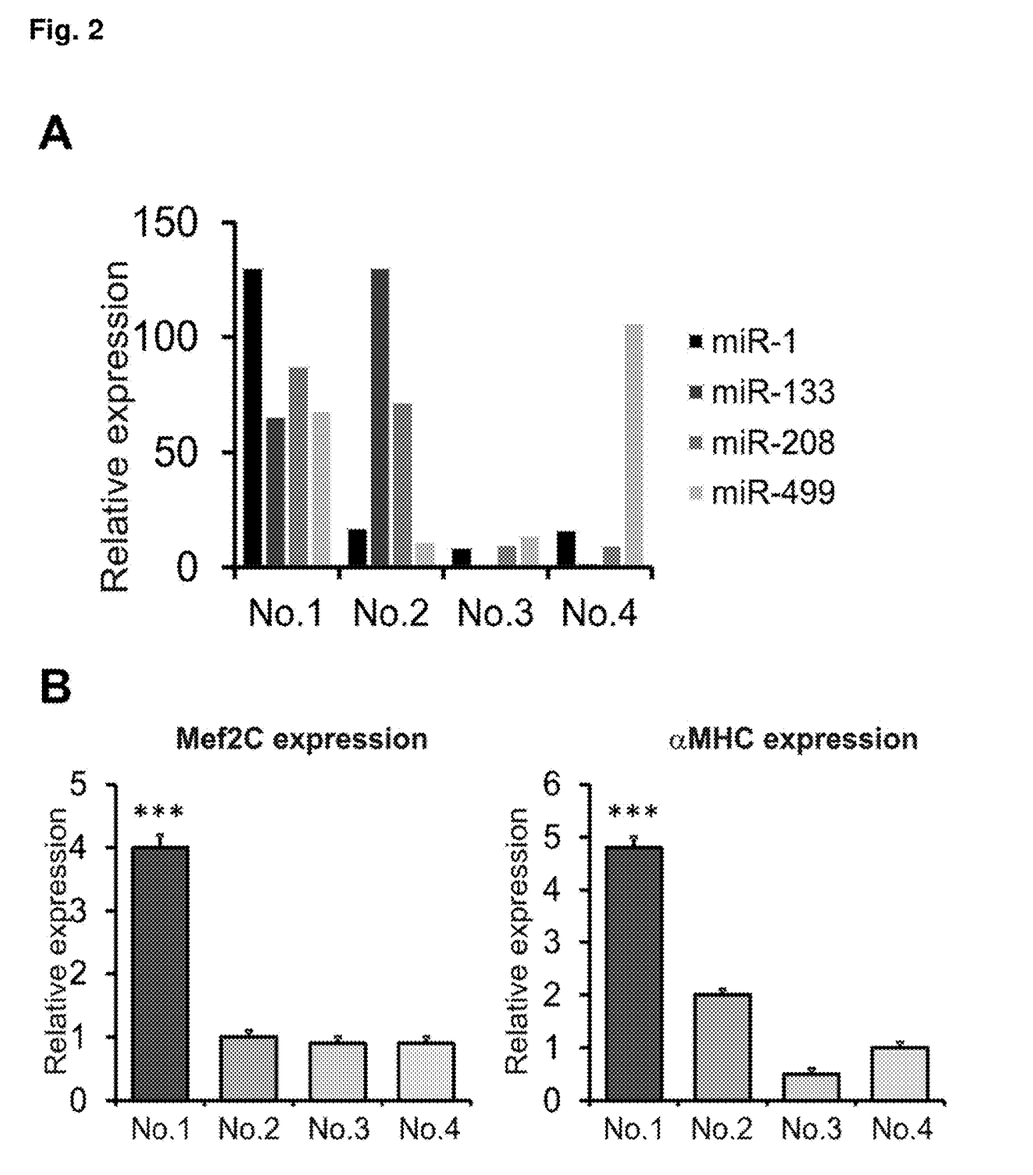

Within vertebrate genomes, miRNA genes tend to be clustered together with clusters transcribed as a single primary transcript which is then cleaved into the mature functional miRNAs(20). These endogenous clusters offer a relatively straightforward template to develop a synthetic multicistronic miRNA construct. The miR-17-92 cluster which produces 7 miRNAs as a primary transcript (21,22) was used (FIG. 1A). This cluster has been utilized previously to deliver miRNAs that target the Hepatitis C virus (18). Importantly, the ordering and placement of the miRNAs in this cluster affected their expression levels. The mature miRNA sequences of miR-17-92 were replaced with those of the constituents of miR combo, keeping the pre-miRNA and linking sequences of the miR-17-92 backbone intact to ensure expression of miRNAs (FIG. 1B). The miR-92a-1 site was deleted entirely as expression of this miRNA is weak (21). To determine if position/stoichiometry of the miRNAs affected expression and reprogramming four multicistronic miR combo constructs were generated and evaluated for their effects in cultured neonatal cardiac fibroblasts (FIG. 1C). Each individual miRNA of miR combo was placed in positions 2 and 5 of the original miR-17-92 multicistronic as it has been demonstrated that these positions give rise to highest miRNA expression of the endogenous miRNAs (18). Each configuration strongly affected the relative expression levels of the four miRNAs in miR combo. Construct number 1, miR-499:miR-1:miR-208: miR-133:miR-1 gave rise to roughly equivalent levels of expression for each miRNA (FIG. 2A). In contrast, other combinations were more selective. Construct 2 (miR-499: miR-133:miR-208:miR-133) strongly induced miR-133 and miR-208 expression only (FIG. 2A). Similarly, construct 4 (miR-208:miR-499:miR-133:miR-1:miR-499) only induced miR-499 (FIG. 2A). Construct 3 (miR-499:miR-208:miR-133:miR-1:miR-499) was unable to induce the expression of any miRNA (FIG. 2A).

The effects of miRNA stoichiometry on reprogramming efficiency was then measured. As shown in FIG. 2B, the positions of the miRNAs within the multicistronic affected the magnitude of reprogramming in vitro. Neonatal cardiac fibroblasts were transfected with the 4 different constructs of miR combo or the non-targeting miRNA construct as a control. After 3 days, RNA was extracted and assayed for cardiac gene expression by qPCR. It was found that construct 1 of miR combo significantly induced the expression of Mef2C and α-MHC (FIG. 2B). In contrast, neither construct 2, construct 3 nor construct 4 were able to induce reprogramming (FIG. 2B).

Figure 3:
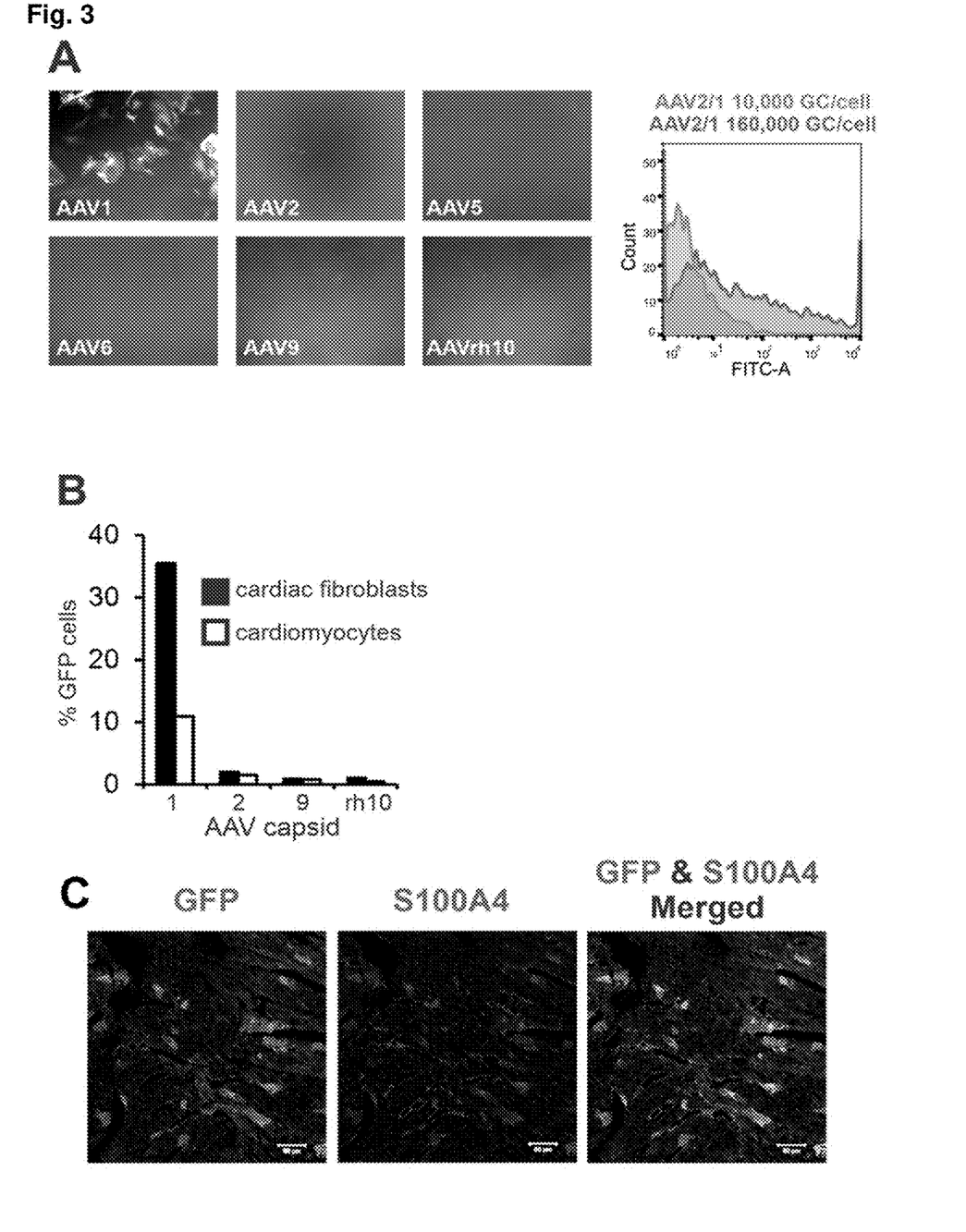

Current strategies to deliver reprogramming factors into the heart utilize *lenti-* and retro-viruses. However, these viruses are not selective; targeting any dividing cell. Efficient cardiac reprogramming requires that reprogramming factors are delivered solely into cardiac fibroblasts. AAVs are an ideal type of agent for cell specificity as various AAV serotypes. Consequently, it was examined if an AAV serotype existed that would exhibit selectivity towards cardiac fibroblasts. To that end, neonatal cardiac fibroblasts were screened in vitro with AAV-GFPs of serotypes 1, 2, 5, 6, 9 and rh10. GFP expression was only observed with fibroblasts infected with the AAV2/1 serotype (FIG. 3A) with a transduction efficiency of 35%. The analysis was repeated with neonatal cardiomyocytes, AAV1 serotype transduction was much lower (~10%) than that observed in the fibroblasts (FIG. 3B). AAV-GFP serotype 1 was injected into non-injured hearts to examine its ability to transduce fibroblasts in vivo. Three weeks later, hearts were removed and the expression of GFP and S100A4 (fibroblast marker) was detected by confocal immunofluorescence. The results demonstrated that in vivo, AAV1 transduced fibroblasts with high efficiency (FIG. 3C).

Figure 4:
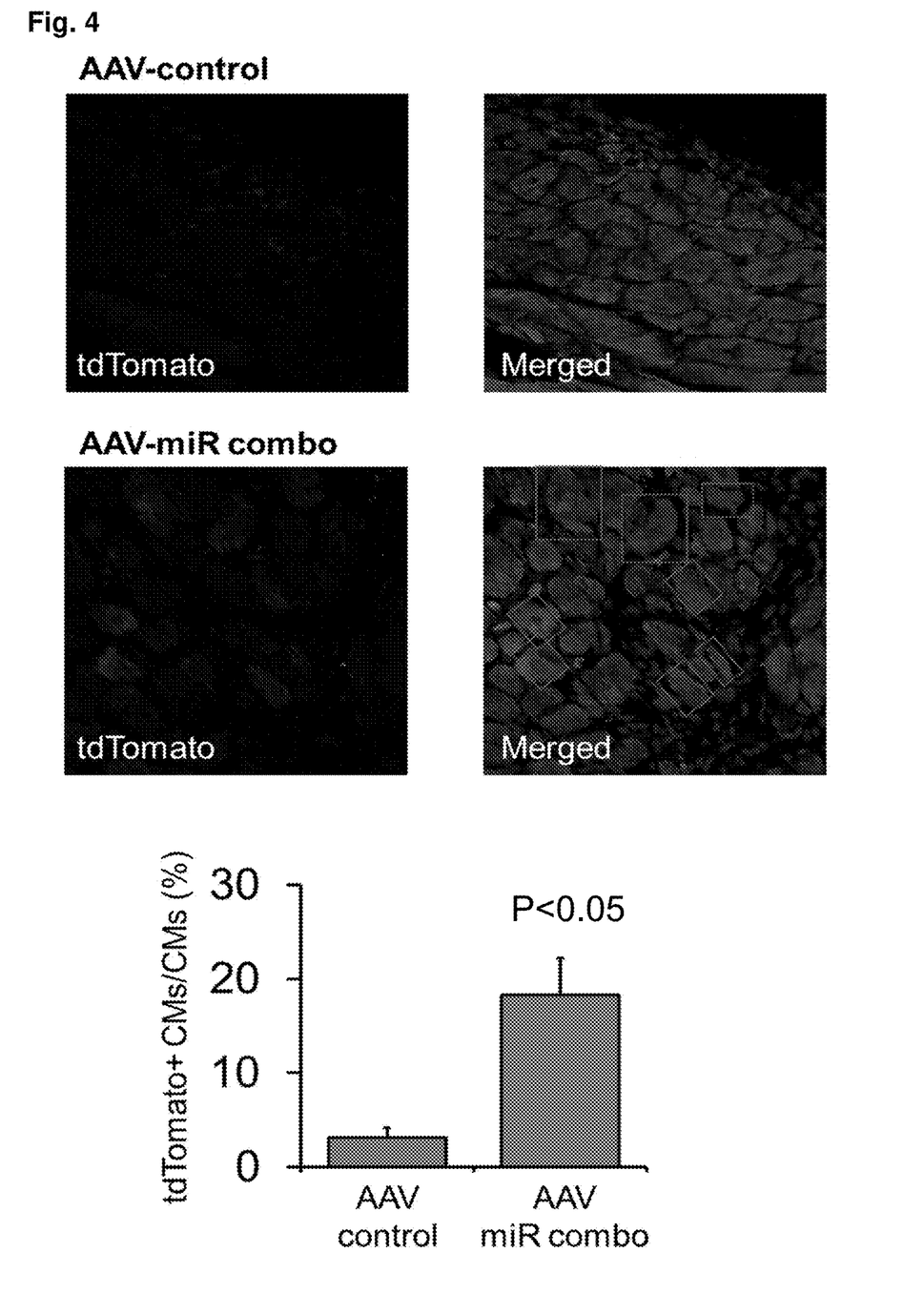
FIG. 4 is a set of graphs showing that a multicistronic miR combo reprograms fibroblasts into cardiomyocytes in vivo. Fibroblast-specific protein 1-Cre/tandem dimer Tomato (tdTomato) mice were subjected to either a sham operation or myocardial infarction (MI). Immediately after MI, a control AAV or a single AAV virus containing construct 1 of the multicistronic miR combo was injected into the heart. An AAV containing a non-targeting miRNA (negmiR) was used as a control. Eight weeks after injury the entire peri-infarct region was visualized by serial sectioning through the heart tissue. Sections were probed for tdTomato and cardiac troponin-T. For all panels, scale bar, 100 μm, n=3, P values indicated.

Following these experiments, the system was tested for its ability to efficiently reprogrammed fibroblasts into cardiomyocytes, due to its delivery of reprogramming factors into cardiac fibroblasts in vivo. The multicistronic miR combo was packaged into the AAV1 and injected into the mouse heart immediately following myocardial infarction. Fibroblast lineage tracing was then employed to track fibroblast conversion into cardiomyocytes. As demonstrated in FIG. 4, delivery of the multicistronic miR combo was efficient in converting fibroblasts into functioning mature cardiomyocytes in vivo (FIG. 4).

Cardiac muscle tissue, or myocardium, is a specialized type of muscle tissue (comprising cardiomyocytes) that forms the heart. And important function of cardiomyocytes is to mediate the beating of the heart, i.e., contraction of cardiac muscle tissue, which contracts and releases involuntarily, and is responsible for keeping the heart pumping blood around the body. The invention described herein is a significant improvement over existing methods and represents an important solution to the problem of reduced/impaired cardiac muscle function in patients who have suffered damage to the heart muscle (e.g., from a heart attack/myocardial infarction or from other injury such as infection such as bacterial or viral infections). Thus, the methods are of great clinical benefit to subjects who have experienced cardiac infarction or other cardiac conditions or events that have led to cardiac scars/fibrosis.

It is commonly thought that low reprogramming efficiency is due to reprogramming barriers. Indeed cell-cycle inhibitors; epigenetic regulators; Wnt/b-catenin pathway components; as well as the failure to activate innate immunity pathways have all been cited as barriers to reprogramming. In contrast, reprogramming factor stoichiometry has received far less attention. This is an important area of research as current methods of reprogramming factor delivery in vivo utilize pools of viruses each expressing one individual reprogramming factor leading to varying relative levels of each reprogramming factor in each transduced cell. The limited stoichiometric analysis conducted to date suggests that reprogramming factor stoichiometry is an underappreciated barrier to reprogramming. Stoichiometric analysis of the OKSM factors for reprogramming to iPS has demonstrated that high Oct4 expression versus modest Klf4 expression is optimal (23,24). Moreover, high Mef2C expression compared to Gata4 and Tbx5 expression increases the efficiency of GMT based fibroblast conversion into cardiomyocytes (14). The data described herein demonstrate that positioning of the miRNAs within a multicistronic influences miRNA based reprogramming outcomes. Equivalent expression levels of the four miRNAs in miR combo were necessary for reprogramming fibroblasts into cardiomyocytes. Disordered miRNA expression, where the expression of a single miRNA dominated, was associated with poor reprogramming efficiency.

The miR combination system was delivered using an AAV vector based approach. Use of AAV vectors allows for delivery of the entire miR combo in a single cassette to target cells, bypassing the need for multiple virus particles encoding transcription factors. AAV serotype 1 showed specific transduction of cardiac fibroblasts in vitro and in vivo, and mediated cardiac fibroblast reprogramming following myocardial infarction. These results lead to AAV-miR combo treatment for injured cardiac tissue regeneration. Rational engineering and directed evolution methods will generate AAV capsid mutants with enhanced cardiac fibroblast transduction efficiencies. Further optimization of miR-combo expressing AAV cassettes leads to optimal stoichiometric miR expression for increased fibroblast reprogramming in vivo.

In conclusion, adjusting reprogramming factor stoichiometry is necessary for efficient cellular reprogramming. The multicistronic miR combo described here solves problem of poor reprogramming efficiency, i.e., the multicistronic miR combo was efficient in converting fibroblasts into functioning mature cardiomyocytes in vivo leading to improved clinical outcomes.

REFERENCES

1. Heidenreich, P. A., Trogdon, J. G., Khavjou, O. A., Butler, J., Dracup, K., Ezekowitz, M.
   D., Finkelstein, E. A., Hong, Y., Johnston, S. C., Khera, A., Lloyd-Jones, D. M., Nelson, S. A., Nichol, G., Orenstein, D., Wilson, P. W., Woo, Y. J., American Heart Association Advocacy Coordinating, C., Stroke, C., Council on Cardiovascular, R., Intervention, Council on Clinical, C., Council on, E., Prevention, Council on, A., Thrombosis, Vascular, B., Council on, C., Critical, C., Perioperative, Resuscitation, Council on Cardiovascular, N., Council on the Kidney in Cardiovascular, D., Council on Cardiovascular, S., Anesthesia, Interdisciplinary Council on Quality of, C., and Outcomes, R. (2011) Forecasting the future of cardiovascular disease in the United States: a policy statement from the American Heart Association. *Circulation* 123, 933-944

2. Fan, D., Takawale, A., Lee, J., and Kassiri, Z. (2012) Cardiac fibroblasts, fibrosis and extracellular matrix remodeling in heart disease. *Fibrogenesis Tissue Repair* 5, 15
3. Hodgkinson, C. P., Kang, M. H., Dal-Pra, S., Mirotsou, M., and Dzau, V. J. (2015) MicroRNAs and Cardiac Regeneration. *Circ Res* 116, 1700-1711
4. Dal-Pra, S., and Mirotsou, M. (2014) Reprogramming approaches in cardiovascular regeneration. *Curr Treat Options Cardiovasc Med* 16, 327
5. Qian, L., Berry, E. C., Fu, J. D., Ieda, M., and Srivastava, D. (2013) Reprogramming of mouse fibroblasts into cardiomyocyte-like cells in vitro. *Nat Protoc* 8, 1204-1215
6. Nam, Y. J., Lubczyk, C., Bhakta, M., Zang, T., Fernandez-Perez, A., McAnally, J., Bassel-Duby, R., Olson, E. N., and Munshi, N. V. (2014) Induction of diverse cardiac cell types by reprogramming fibroblasts with cardiac transcription factors. *Development* 141, 4267-4278
7. Jayawardena, T. M., Egemnazarov, B., Finch, E. A., Zhang, L., Payne, J. A., Pandya, K., Zhang, Z., Rosenberg, P., Mirotsou, M., and Dzau, V. J. (2012) MicroRNA-mediated in vitro and in vivo direct reprogramming of cardiac fibroblasts to cardiomyocytes. *Circ Res* 110, 1465-1473
8. Jayawardena, T. M., Finch, E. A., Zhang, L., Zhang, H., Hodgkinson, C. P., Pratt, R. E., Rosenberg, P. B., Mirotsou, M., and Dzau, V. J. (2015) MicroRNA induced cardiac reprogramming in vivo: evidence for mature cardiac myocytes and improved cardiac function. *Circ Res* 116, 418-424
9. Hodgkinson, C. P., Pratt, R. E., Kirste, I., Dal-Pra, S., Cooke, J. P., and Dzau, V. J. (2018) Cardiomyocyte Maturation Requires TLR3 Activated Nuclear Factor Kappa B. *Stem Cells* 36, 1198-1209
10. Qian, L., Huang, Y., Spencer, C. I., Foley, A., Vedantham, V., Liu, L., Conway, S. J., Fu, J. D., and Srivastava, D. (2012) In vivo reprogramming of murine cardiac fibroblasts into induced cardiomyocytes. *Nature* 485, 593-598
11. Song, K., Nam, Y. J., Luo, X., Qi, X., Tan, W., Huang, G. N., Acharya, A., Smith, C. L., Tallquist, M. D., Neilson, E. G., Hill, J. A., Bassel-Duby, R., and Olson, E. N. (2012) Heart repair by reprogramming non-myocytes with cardiac transcription factors. *Nature* 485, 599-604
12. Okita, K., Ichisaka, T., and Yamanaka, S. (2007) Generation of germline-competent induced pluripotent stem cells. *Nature* 448, 313-317
13. Papapetrou, E. P., Tomishima, M. J., Chambers, S. M., Mica, Y., Reed, E., Menon, J., Tabar, V., Mo, Q., Studer, L., and Sadelain, M. (2009) Stoichiometric and temporal requirements of Oct4, Sox2, Klf4, and c-Myc expression for efficient human iPSC induction and differentiation. *Proc Natl Acad Sci USA* 106, 12759-12764
14. Wang, L., Liu, Z., Yin, C., Asfour, H., Chen, O., Li, Y., Bursac, N., Liu, J., and Qian, L. (2015) Stoichiometry of Gata4, Mef2c, and Tbx5 influences the efficiency and quality of induced cardiac myocyte reprogramming. *Circ Res* 116, 237-244
15. Milone, M. C., and O'Doherty, U. (2018) Clinical use of lentiviral vectors. *Leukemia* 32, 1529-1541
16. Chamberlain, K., Riyad, J. M., and Weber, T. (2017) Cardiac gene therapy with adeno-associated virus-based vectors. *Curr Opin Cardiol*
17. McCarty, D. M. (2008) Self-complementary AAV vectors; advances and applications. *Mol Ther* 16, 1648-1656
18. Yang, X., Haurigot, V., Zhou, S., Luo, G., and Couto, L. B. (2010) Inhibition of hepatitis C virus replication using adeno-associated virus vector delivery of an exogenous anti-hepatitis C virus microRNA cluster. *Hepatology* 52, 1877-1887
19. Jayawardena, T., Mirotsou, M., and Dzau, V. J. (2014) Direct reprogramming of cardiac fibroblasts to cardiomyocytes using microRNAs. *Methods Mol Biol* 1150, 263-272
20. Altuvia, Y., Landgraf, P., Lithwick, G., Elefant, N., Pfeffer, S., Aravin, A., Brownstein, M. J., Tuschl, T., and Margalit, H. (2005) Clustering and conservation patterns of human microRNAs. *Nucleic Acids Res* 33, 2697-2706
21. Lu, Y., Thomson, J. M., Wong, H. Y., Hammond, S. M., and Hogan, B. L. (2007) Transgenic over-expression of the microRNA miR-17-92 cluster promotes proliferation and inhibits differentiation of lung epithelial progenitor cells. *Dev Biol* 310, 442-453
22. Mogilyansky, E., and Rigoutsos, I. (2013) The miR-17/92 cluster: a comprehensive update on its genomics, genetics, functions and increasingly important and numerous roles in health and disease. *Cell Death Differ* 20, 1603-1614
23. Tiemann, U., Sgodda, M., Warlich, E., Ballmaier, M., Scholer, H. R., Schambach, A., and Cantz, T. (2011) Optimal reprogramming factor stoichiometry increases colony numbers and affects molecular characteristics of murine induced pluripotent stem cells. *Cytometry A* 79, 426-435
24. Carey, B. W., Markoulaki, S., Hanna, J. H., Faddah, D. A., Buganim, Y., Kim, J., Ganz, K., Steine, E. J., Cassady, J. P., Creyghton, M. P., Welstead, G. G., Gao, Q., and Jaenisch, R. (2011) Reprogramming factor stoichiometry influences the epigenetic state and biological properties of induced pluripotent stem cells. *Cell Stem Cell* 9, 588-598

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A method of promoting reprogramming of a cardiac fibroblast into a cardiomyocyte by contacting the cardiac fibroblast with an isolated polynucleotide molecule comprising functional miRNAs: miR-1, miR-133, miR-208, and miR-499, wherein said functional miRNAs are arranged in a 5' to 3' orientation as an ordered combination of miR-499:miR-1:miR-208:miR-133:miR-1 in an miR-17-92 backbone, and wherein the mature miRNAs of the miR-17-92 backbone are replaced by said functional miRNAs.

2. The method of claim 1, wherein the cardiac fibroblast is contacted with the isolated polynucleotide molecule in vivo.

3. The method of claim 1, wherein the cardiac fibroblast is in a human subject diagnosed with impaired cardiac function.

4. The method of claim 1, wherein the cardiac fibroblast is in a human subject diagnosed with the presence of cardiac scar tissue.

5. The method of claim 1, wherein the isolated polynucleotide molecule comprises a multicistronic system to express said miRNAs, and wherein the multicistronic system is expressed in a cardiac-tropic adeno-associated virus (AAV)-based vector.

6. The method of claim 1, wherein said miR-17-92 backbone comprises pre-miRNA sequences and linking sequences of miR-17-92.

7. The method of claim 1, wherein said miR-17-92 backbone lacks miR-92a-1 pre-miRNA sequence.

8. The method of claim 1, wherein said miR-1 has the sequence of SEQ ID NO: 6.

9. The method of claim 1, wherein said miR-133 has the sequence of SEQ ID NO:7.

10. The method of claim 1, wherein said miR-208 has the sequence of SEQ ID NO:8.

11. The method of claim 1, wherein said miR-499 has the sequence of SEQ ID NO:9.

* * * * *